United States Patent [19]

Ives

[11] Patent Number: 4,619,915
[45] Date of Patent: Oct. 28, 1986

[54] PEPTIDE-SUBSTITUTED HETEROCYCLIC IMMUNOSTIMULANTS

[75] Inventor: Jeffrey L. Ives, Guilford, Conn.

[73] Assignee: Pfizer Inc., New York, N.Y.

[21] Appl. No.: 662,668

[22] Filed: Oct. 19, 1984

[51] Int. Cl.$^4$ .............. A61K 37/02; C07K 7/02; C07K 5/06; C07K 5/08; C07K 5/10

[52] U.S. Cl. ........................... 514/17; 514/18; 514/19; 530/330; 530/331; 530/332

[58] Field of Search .................. 260/112.5 R; 514/17, 514/18, 19; 530/330, 331, 332

[56] References Cited

U.S. PATENT DOCUMENTS 4,322,341 3/1982 Kitaura et al. ............ 260/112.5 R
4,427,581 1/1984 Miyazaki et al. ........... 260/112.5 R

OTHER PUBLICATIONS

Kitaura et al., J. Med. Chem., 25, 335–337 (1982).

Primary Examiner—Delbert R. Phillips
Attorney, Agent, or Firm—Charles J. Knuth; Albert E. Frost; Peter C. Richardson

[57] ABSTRACT

Peptide-substituted heterocyclic compounds having the formula below, pharmaceutically acceptable salts thereof and intermediates therefor; processes for their preparation and use as immunostimulant and antiinfective agents.

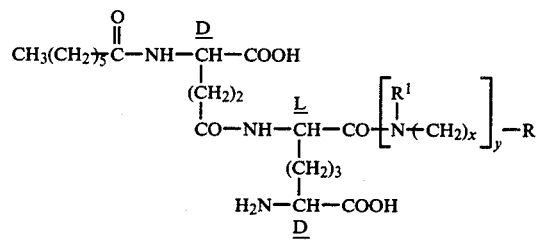

wherein R is a 5- or 6-membered N-containing heterocyclyl moiety which can have an additional hetero atom selected from N, S or O; $R^1$ is hydrogen or ($C_{1-4}$)alkyl; x is 0 or an integer from 1 to 5; and y is 0 or 1; provided that when y is 0, said N-containing heterocyclyl moiety is linked to the

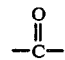

group at its N atom.

18 Claims, No Drawings

PEPTIDE-SUBSTITUTED HETEROCYCLIC IMMUNOSTIMULANTS

BACKGROUND OF THE INVENTION

1. Field of the Invention

This invention relates to novel peptide-substituted heterocyclic compounds useful as immunostimulant and antiinfective agents; to pharmaceutically acceptable salts thereof; to intermediates therefor and to processes for their preparation.

2. Description of the Prior Art

The relatively new field of immunopharmacology, and particularly that segment thereof which deals with immunomodulation, continues to develop at a rapid pace. A variety of naturally occurring compounds has been investigated, including the tetrapeptide tuftsin, known chemically as $N^2$-[1-($N^2$-L-threonyl-L-lysyl)-L-prolyl]-L-arginine. Much attention has been directed to synthetic peptidoglycan derivatives, especially those known as muramyl dipeptides. For summaries of the wide range of compounds investigated as immunomodulators, and especially as immunostimulants, attention is directed to Dukar et al., Annu. Rep. Med. Chem., 14, 146–167 (1979), Lederer, J. Med. Chem., 23, 819–825 (1980) and to J. Kralovec, Drugs of the Future, 8, 615–638 (1983).

Immunostimulant peptides have been described in a number of patent specifications:

L-Alanyl-alpha-glutaric acid N-acyl dipeptides in German No. 3,024,355, published Jan. 15, 1981;

tetra- and penta-peptides containing D-alanyl-L-glutamyl moieties or L-alanyl-D-glutamyl moieties in British No. 2,053,231, published Feb. 4, 1981 and German No. 3,024,281, published Jan. 8, 1981, respectively; and N-acyl-L-alanyl-gamma-D-glutamyl tripeptide derivatives in which the C-terminal amino acid is lysine or diaminopimelic acid in German No. 3,024,369, published Jan. 15, 1981; and lactyl tetrapeptides composed of N-lactylalanyl, glutamyl, diaminopimelyl and carboxymethylamino components in EP-11283, published May 28, 1980.

Further immunostimulant polypeptides having the formula (A)

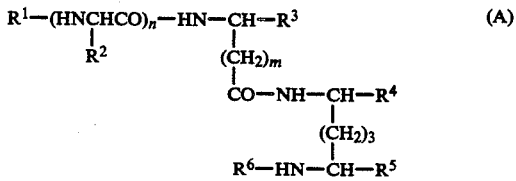

wherein $R_1$ is hydrogen or acyl; $R^2$ is inter alia hydrogen, lower alkyl, hydroxymethyl, benzyl; $R^3$ and $R^4$ are each hydrogen, carboxy, $-CONR^7R^8$ wherein $R^7$ is hydrogen, lower alkyl optionally substituted with hydroxy; and $R^8$ is mono- or dicarboxy lower alkyl; $R^5$ is hydrogen or carboxy with the proviso that when one of $R^4$ and $R^5$ is hydrogen, the other is carboxy or $-CONR^7R^8$; $R^6$ is hydrogen; m is 1 to 3 and n is 0 to 2, and derivatives thereof in which the carboxy and amino groups are protected are disclosed in U.S. Pat. Nos. 4,311,640 and 4,322,341; EP applications 25,482; 50,856; 51,812; 53,388; 55,846 and 57,419.

None of the polypeptides disclosed in the art has a heterocyclyl containing amino acid moiety at the position occupied by variable $R^4$ in the above formula. U.S. application Ser. No. 595,169, filed Mar. 30, 1984 by Ives et al., describes polypeptides wherein variable $R^4$ is a basic amino acid moiety.

Kitaura et al., J. Med. Chem, 25, 335–337 (1982) report $N^2$-(gamma-D-glutamyl)-meso-2(L),2'(D)-diaminopimelic acid as the minimal structure capable of eliciting a biological response characteristic of the compound of formula (A) wherein n is 1; $R^1$ is $CH_3CH(OH)-CO-$; $R^2$ is $CH_3$; each of $R^3$ and $R^5$ is $-COOH$; $R^4$ is $-CONHCH_2COOH$; and $R^6$ is H. Said compound of formula (A) is known as FK-156.

SUMMARY OF THE INVENTION

Novel compounds of formula (I)

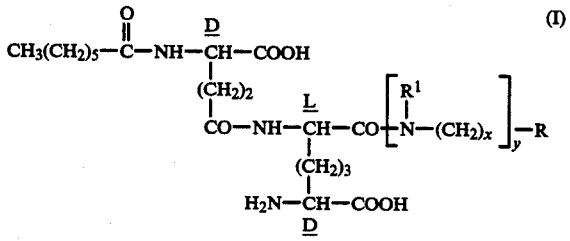

and pharmaceutically acceptable salts thereof are efficient immunostimulants or immunomodulators, and antiinfective agents. In the above formula:

R is an unsubstituted or substituted 5- or 6-membered heterocyclyl moiety selected from the group consisting of those heterocyclyl moieties having (a) one N atom,
(b) two N atoms,
(c) one N and one O atom or
(d) one N and one S atom;

and wherein the substituent is selected from the group consisting of methyl, oxo, carboxy or carbo ($C_{1-4}$alkoxy);

$R^1$ is hydrogen or ($C_{1-2}$)alkyl;

x is 0 or an integer from 1 to 5; and y is 0 or 1; provided that when y is 0, said heterocyclyl moiety is linked to the $-CO-$ group at its N atom.

By pharmaceutically acceptable salts of said compounds of formula (I) is meant salts with inorganic or organic bases such as alkali metal, alkaline earth metal, ammonium, triethylamine, ethanolamine, dicyclohexylamine salts; and acid addition salts with organic and inorganic acids, such as methanesulfonic, p-toluenesulfonic acids, hydrogen chloride, hydrogen bromide, phosphoric, sulfonic and the like.

The configuration of the amino acid moieties which make up the formula (I) compounds is significant as regards the pharmacological activity of said compounds. The most potent activity is observed in formula (I) compounds having the stereochemistry indicated in said formula. The stereochemistry, relative to that of the natural amino acids, is designated as D- or L-.

Favored compounds of formula (I) are those wherein R is a 5- or 6-membered heterocyclyl moiety containing two N atoms or one N and one O atom; and those compounds wherein y is 1; x is an integer from 1 to 5; and $R^1$ is hydrogen. Preferred compounds are those wherein y is 1; x is from 1 to 4; $R^1$ is hydrogen and R is a substituted heterocyclyl moiety. An especially preferred compound is the formula (I) compound wherein y is 1; x is 4; $R^1$ is hydrogen and R is 5-L-hydantoin.

The compounds of formula (I) are prepared by any of several methods known to those skilled in the art. The methodology involves the formation of peptide linkages between amino acids which, because of their amino and carboxy groups, and frequently the presence of other reactive groups, necessitate the protection of said groups and/or the activation of such groups, particularly the carboxy group, in order to achieve a certain reaction or to optimize such a reaction.

The overall reaction sequence involved is shown below.

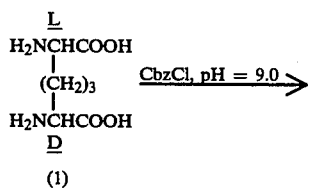
(1)

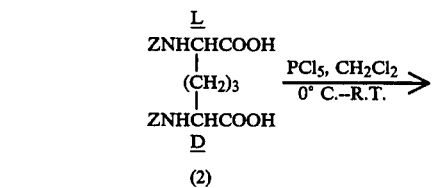
(2)

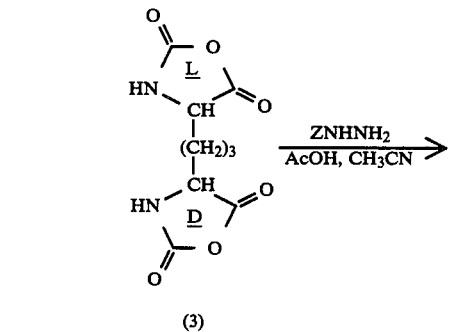
(3)

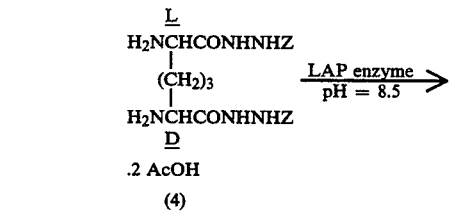
.2 AcOH
(4)

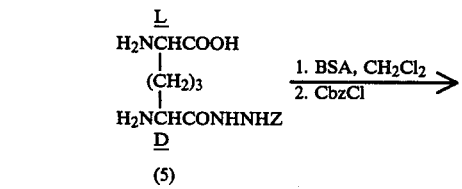
(5)

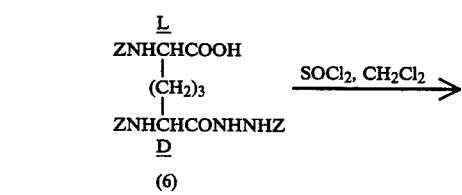
(6)

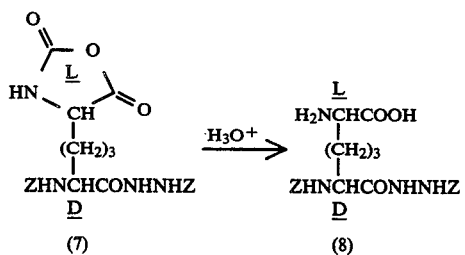
(7)  (8)

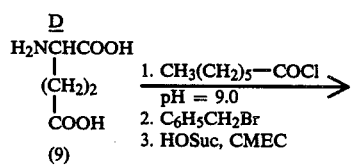
(9)

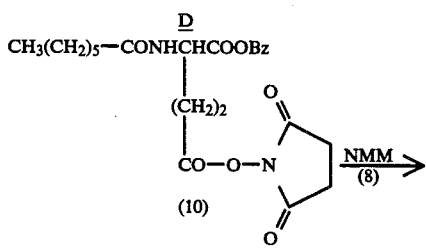
(10)

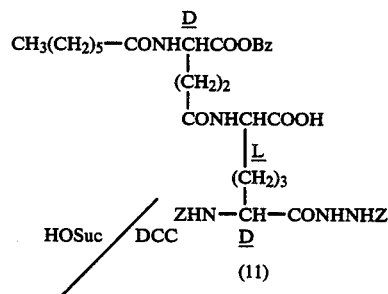
(11)

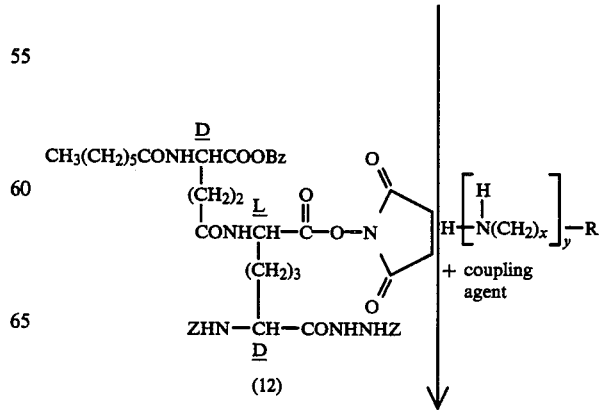
(12)

-continued

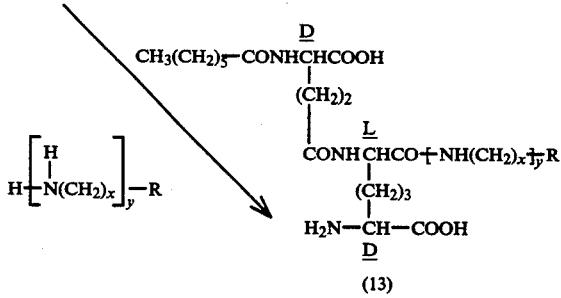

Z=Cbz=benzyloxycarbonyl
BSA=bis-trimethylsilylacetamide
CMEC=1-cyclohexyl-3-(2-morpholinoethyl)carbodiimide metho-p-toluene sulfonate
HOSuc=N-hydroxysuccinimide
NMM=N-methylmorpholine
n, x, y and R=as defined herein
DCC=dicyclohexylcarbodiimide As is evident from the above reaction sequence, the amino acids which make up the compound of formula (I) are prepared by joining the acylated glutamic acid to the diaminopimelic acid-lysine (or basic amino acid) dipeptide moiety. The dipeptide moiety is, in turn, prepared by joining diaminopimelic acid to lysine as per the above sequence. The order in which the individual amino acids are combined to produce the tripeptide is immaterial.

In the examples presented herein, certain protecting and activating groups are specifically illustrated. However, one skilled in the art will recognize that other protecting or activating groups could have been used. The choice of a particular protecting group is dependent to a great extent upon the availability of the necessary reagent, its effect upon solubility of the "protected" compound, its ease of removal and the presence of other groups which might be effected by its use; i.e. its selectivity, or its removal.

For example, it will be necessary, or at least desirable, in many reactions to protect the amino groups and/or the carboxy groups. The synthetic route chosen for the peptide synthesis may require removal of one or the other or both of said protecting groups in order to permit further reaction at the regenerated amino or carboxy group; i.e., the protecting groups used are reversible and, in most instances, are removable independently of each other. Additionally, the choice of protecting group for a given amino group depends upon the role of said amino group in the overall reaction scheme. Amino protecting groups having varying levels of lability, i.e., ease of removal, will be used. The same is true as regards carboxy protecting groups. Such groups are known in the art and attention is directed to the reviews by Bodansky et al., "Peptide Synthesis", 2nd Ed., John Wiley & Sons, N.Y. (1976); Greene, "Protective Groups in Organic Synthesis", John Wiley & Sons, N.Y. (1981); McOmie, "Protective Groups in Organic Chemistry", Plenum Press, N.Y. (1973); and to Sheppard in "Comprehensive Organic Chemistry, The Synthesis and Reactions of Organic Compounds", Pergaman Press, N.Y. (1979), edited by E. Haslam, Part 23.6, pages 321–339.

Conventional amino and carboxy protecting groups are known to those skilled in the art. Representative amino protecting groups, but by no means limiting thereof, are the following: such as benzyloxycarbonyl; substituted or unsubstituted aralkyl such as benzyl, trityl, benzhydryl and 4-nitrobenzyl; benzylidene; arylthio such as phenylthio, nitrophenylthio and trichlorophenylthio; phosphoryl derivatives such as dimethylphosphoryl and O,O-dibenzylphosphoryl; trialkylsilyl derivatives such as trimethylsilyl; and others as are described in U.S. Pat. No. 4,322,341 and which are incorporated herein by reference. The preferred amino protecting group is benzyloxycarbonyl. Procedures for substituting said group on a given amino group are well known. In general they comprise acylating the appropriate amino compound with benzyloxycarbonyl chloride (benzylchloroformate) in a reaction-inert solvent, e.g., water, methylene chloride, tetrahydrofuran, in the presence of a base (acid acceptor) e.g. sodium or potassium hydroxide when water is solvent; and, when an organic solvent is used, in the presence of a tertiary amine such as $C_{1-4}$ trialkylamines and pyridine. When an aqueous solvent system is used the pH of the reaction is held at about pH 8–10, and preferably at pH 9. Alternatively, when the reactant; i.e., the compound, an amino group of which is to be protected, contains basic groups, it can serve as acid acceptor.

The acyl group, $CH_3(CH_2)_nCO$, is introduced into the glutamic acid reactant (compound 9 in the above sequence) by standard acylation procedures as by reacting said glutamic acid with the appropriate acid chloride or bromide in a reaction inert solvent. Favored conditions are aqueous systems, e.g., aqueous acetone, and a pH of 9.0, the pH being maintained at 8.5–9.0 by addition of a suitable base such as sodium or potassium hydroxide. Non-aqueous solvents can also be used. However, in such instances an organic base, preferably a tertiary amine such as triethylamine, N-methylmorpholine or pyridine is used as base.

The acylation can, of course, be accomplished by means of the appropriate acid anhydride (simple or mixed) according to standard procedures. When an anhydride is to be used for this acylation step, mixed anhydrides especially those derived from a low molecular weight carboxylic acid, and particularly the mixed carboxylic-carbonic anhydrides, are favored.

The nature of the acyl group is not critical to this invention and acyl groups having from 2–7 carbon atoms are fully operative in this invention. The heptanoyl group, $CH_3(CH_2)_5CO—$, is a favored group particularly as regards compounds having formula (I) wherein y is 0 or wherein R is a hydantoin moiety.

The $R^1$ variable in formula (I) compounds is not critical but can also range to alkyl groups having up to 4 carbon atoms. However, from the standpoint of availability of reactants, compounds wherein $R^1$ is hydrogen or $C_{1-2}$alkyl are favored.

Representative carboxy protecting groups are various esters such as silyl esters, including trialkyl silyl esters, trihalosilyl esters and haloalkylsilyl esters; certain hydrocarbyl esters such as $C_{1-4}$ alkyl, especially t-butyl groups; benzyl and substituted benzyl esters, benzhydryl and trityl; phenacyl and phthalimidomethyl esters; certain substituted hydrocarbyl esters such as chloromethyl, 2,2,2-trichloroethyl, cyanomethyl; tetrahydropyranyl; methoxymethyl; methylthiomethyl; protected carbazoyl such as —CONH—NHR° wherein R° is an amino protecting group as disclosed above, especially benzyloxycarbonyl; and others as are described in U.S. Pat. No. 4,322,341 and which are incorporated herein by reference. The preferred carboxy protecting group is —CONH—NHR° wherein R° is benzyloxycarboxyl, said preferred group being referred to as benzyloxycarbonylcarbazide. A highly favored carboxy protecting group is the benzyl group.

The protected amino and carboxy groups are converted to the unprotected amino and carboxy groups by procedures known to those skilled in the art. The benzyloxycarbonyl group and the benzyl group, the preferred protecting groups for amino and carboxy (as part of the protected carbazoyl group) groups are removed by catalytic hydrogenation over palladium, especially palladium-on-carbon. Alternatively, said protecting groups are removed by means of trifluoromethanesulfonic acid in trifluoroacetic acid and in the presence of anisole to suppress alkylation.

Selected removal of one benzyloxycarbonylcarbazide protecting group from meso-diaminopimelic acid dibenzyloxycarbonylcarbazide (product of Example 3 below) is conveniently accomplished by means of leucine aminopeptidase (LAP). The reaction is conducted in an aqeuous solvent, especially in a mixture of water and a water miscible solvent (such as a $C_{1-4}$ alkanol, tetrahydrofuran, dioxane) at an alkaline pH, the pH range of 8–10 being favored; and a value of 8.5 being preferred.

Activation of carboxy groups as a means of expediting a given reaction is methodology known to those skilled in the art. Especially useful in the herein described reaction sequence are the use of anhydrides, particularly cyclic anhydrides; and activated esters, such as those derived from N-hydroxyphthalimide and N-hydroxysuccinimide, both of which are used in peptide syntheses.

In the herein described reaction sequence, intermediate compounds of formulae (2) and (6) contain alpha-substituted glycine moieties and are conveniently transformed to 2,5-oxazolidinedione derivatives (N-carboxy anhydrides) of formulae (3) and (7), respectively. Said anhydrides facilitate the subsequent reactions to which the formulae (3) and (7) compounds are subjected. They are formed by reacting the amino acid precursors of formulae (2) and (6) with a reagent such as $PCl_5$ or $SOCl_2$.

The activated N-hydroxysuccinimide esters [e.g., formula (10) and (12)]expedite subsequent reactions at said activated ester groups. As the skilled artisan will recognize other activating groups could be used. A group of particular interest is the N-hydroxyphthalimido group, which group is used in the same manner as is the N-hydroxysuccinimido group. In both instances, a dehydrative coupling agent is used to form the activated ester. Representative of such coupling agents are 1-cyclohexyl-3-(2-morpholinoethyl)carbodiimide method-p-toluene sulfonate, dicyclohexyl carbodiimide, N,N'-carbonyldiimidazole, N-(3-dimethylaminopropyl)-N'-ethylcarbodiimide hydrochloride, ethoxyacetylene, diphenylketene and N-ethyl-5-phenylisoxazoliene-3'-sulfonate. The reaction conditions for using such coupling agents are well described in the literature. In general they comprise the use of a reaction-inert solvent and temperatures ranging from ambient to 100° C. The above-mentioned carbodiimide reagents are favored since they permit use of ambient reaction temperature and afford satisfactory yields of the desired esters.

The final products of formula (13) are readily prepared from compounds of formula (11) or of formula (12) by reaction of said compounds with the appropriate amine $H[N(R^1)(CH_2)_x]_y$-R wherein R, $R^1$, x and y are as defined above. The reaction with formula (11) compounds is conducted in the presence of a coupling agent such as those enumerated above and in a reaction-inert solvent at from 0°–30° C. The addition of 1-hydroxybenzotriazole to the reaction, generally in equimolar amount to the amine reactant, serves to improve the yield of the desired condensation product.

Conversion of the activated esters of formula (12) to final products of formula (13) is accomplished by reacting said activated ester with the appropriate amine $H[N(R^1)(CH_2)_x]_y$-R as defined above in a reaction-inert solvent at from 0° to 30° C. in the presence of 1-hydroxybenzotriazole, generally from about 0.1 to 0.2 moles per mole of said amine reactant.

The protected formula (13) compounds thus obtained are then subjected to hydrogenation over palladium-on-carbon in aqueous acetic acid to remove the carboxy and amino protecting groups according to known procedures; or to reaction with trifluoromethanesulfonic acid.

The pharmaceutically acceptable salts of formula (I) compounds are obtained by treating a solution, preferably aqueous solution, thereof with a base or acid, such as are enumerated above, generally in stoichiometric proportions. The salts are isolated by evaporation or by precipitation.

The products of this invention are useful as agents in mammals, including humans, for the clinical and therapeutic treatment of diseases caused by various pathogenic microorganisms, especially gram-negative bacteria. They are also useful as immuno-stimulants in mammals, including humans, having an increased risk of infection due to existing or clinically-induced immunosuppression.

The test procedure, which uses $C_3H/HeN$ male mice from the Charles River Breeding Laboratory, is presented below. The mice were acclimatized for 5 days before use and then treated either subcutaneously (SC) or orally (PO) with various dilutions (10, 1 and 0.1 mg/kg) of the test compound or placebo (pyrogen free saline) using a volume of 0.2 ml. The treatment regimen was dependent on the infectious organism utilized: −24 and 0 hours before challenge for *Klebsiella pneumoniae*; and −6, −5, −4 and −1 day before challenge for *Escherichia coli* or *Pseudomonas aeruginosa*. Challenge was administered intramuscularly (IM) in the hip in the case of *K. pneumoniae* or intraperitoneally (IP) in the case of *E. coli* and *P. aeruginosa*. A volume of 0.2 ml was used for the challenge. Mortality was recorded after 7 days in the case of *K. pneumoniae* and after 3 days in the case of the other two microorganism challenges.

Culture Preparation;

*K. pneumoniae:* the culture was streaked for purity from frozen blood stock on brain heart infusion (BHI) agar. Three colonies were picked from the 18 hour plate culture and placed into 9 ml of BHI broth. The broth culture was grown for 2 hours at 37° C. on a rotary shaker after which 0.2 ml was streaked on the surface of several BHI agar slants. Following an 18 hour incubation at 37° C., the slants were washed with BHI broth, the culture density adjusted using a spectronic 20 and the appropriate dilution made to achieve an LD100 challenge level in mice (approx. 250 CFU/animal). (CFU=Colony forming units). *E. coli* or *P. aeruginosa:* The culture was streaked for purity on the surface of a BHI agar plate from frozen blood stock. Following overnight incubation, several colonies were placed into 100 ml of Difco nutrient agar contained in a 250 ml Erlenmeyer flask. Following an 18 hour incubation at 30° C. on a New Brunswick rotary shaker, a 1:10 dilution was made into 90 ml of fresh nutrient broth. The culture was incubated at 30° C. (rotary shaker, 200 rpm) for 3 hours, the density adjusted to 78% using a spectronic 20, and the appropriate dilution made into BHI broth to achieve an LD90 by intraperitoneal injection into mice.

When used as antiinfective or immunostimulant agents in humans, the compounds of this invention are conveniently administered via the oral, subcutaneous, intramuscular, intravenous or intraperitoneal routes, generally in composition form. Such compositions include a pharmaceutical carrier selected on the basis of the chosen route of administration and standard pharmaceutical practice. For example, they can be administered in the form of tablets, pills, powders or granules containing such excipients as starch, milk sugar, certain types of clay, etc. They can be administered in capsules, in admixtures with the same or equivalent excipients. They can also be administered in the form of oral suspensions, solutions, emulsions, syrups and elixirs which may contain flavoring and coloring agents. For oral administration of the therapeutic agents of this invention, tablets or capsules containing from about 50 to about 500 mg are suitable for most applications.

The physician will determine the dosage which will be most suitable for an individual patient and it will vary with the age, weight and response of the particular patient and the route of administration. Generally, however, the initial dosage in adults may range from about 2-100 mg/kg per day in single or divided doses. The favored oral dosage range is from about 10 to about 300 mg/kg/day. The favored parenteral dose is from about 1.0 to about 100 mg/kg/day; the preferred range from about 1.0 to about 20 mg/kg/day.

This invention also provided pharmaceutical compositions, including unit dosage forms, valuable for the use of the herein described compounds for the utilities disclosed herein. The dosage form can be given in single or multiple doses, as previously noted, to achieve the daily dosage effective for a particular utility.

EXAMPLE 1

N,N'-Dibenzyloxycarbonyl-meso-diaminopimelic acid

To a solution of 209.4 g (1.1 mol) of mesodiaminopimelic acid in 2,200 ml of water, basified to pH 9.0 with 2N sodium hydroxide and cooled on an ice bath to 10° C., was added 450.5 g (2.64 mol) of benzylchloroformate over a 30 minute period. The pH was maintained throughout the addition at 9.0 with 2N sodium hydroxide. After 2.5 hours, the solution was extracted three times with one liter of ethyl acetate. The aqueous solution was acidified with 10% hydrochloric acid to pH 1.5 and extracted twice with one liter of ethyl acetate. The extracts were combined, dried over magnesium sulfate, filtered and concentrated, and the resulting oil was crystallized from 920 ml of chloroform at room temperature to yield 170 g (34%) of the title product: mp 129°–133° C. IR (KBr) 2700, 1720, 1600 cm$^1$; NMR (D$_6$-DMSO) delta 7.1–7.4 (m, 10H), 5.2 (s, 4H), 4.0–4.2 (m, 2H), 1.2–1.6 (m, 6H); [alpha]$_D$=0.0 (C=1.2, MeOH).

EXAMPLE 2 meso-Diaminopimelic acid-di-N-carboxyanhydride

A suspension of 62.0 g (140 mmol) of N,N-dibenzyloxycarbonyl-meso-diaminopimelic acid in 1,240 ml dry methylene chloride was cooled under nitrogen atmosphere to 10° C. and treated in a single portion with 62.0 g (300 mmol) phosphorous pentachloride. The resulting yellow solution was stored one hour at 10° C. and allowed to warm to room temperature for 20 hours. The resulting suspension was filtered, the product washed successively with dry methylene chloride and dried under high vacuum to yield 29.9 g (91%) of the di-N-carboxyanhydride: mp 280° C. IR (KBr) 3250, 1840, 1760 cm$^{-1}$; NMR (D$_6$-DMSO) delta 4.2–4.4 (m, 2H), 1.2–2.0 (m, 6H).

EXAMPLE 3 meso-Diaminopimelic acid-dibenzyloxycarbonylcarbazide diacetate

A stirred solution of 1.4 g (8.5 mmol) of benzyl carbazate in 4 ml of glacial acetic acid was cooled to 10° C., and the resulting slush was treated with 1.0 g (4.1 mmol) of meso-diaminopimelic acid-di-N-carboxyanhydride. The reaction was allowed to warm slowly to room temperature for two hours and the resulting oil triturated with ether to yield 2.37 g (95%) of the title product: mp 158-161° C. IR(Nujol) 2850, 1700 cm$^{-1}$; NMR (CD$_3$OD) delta 7.30 (s, 10H), 5.10 (s, 4H), 3.30 (m, 2H), 1.5–1.8 (m, 6H).

EXAMPLE 4 meso-Diaminopimelic acid-(D)-mono-benzyloxycarbonyl carbazide

A solution of 26.2 g (43 mmol) of meso-diaminopimelic acid-dibenzyloxycarbonylcarbazide diacetate in 325 ml of methanol and 750 ml of water was treated with 2N sodium hydroxide to pH 8.5. The resulting solution was treated with 2,200 units of leucine aminopeptidase (Sigma Hog Kidney, Type III suspension, Sigma Chemical Company, St. Louis, Mo, U.S.A.) and stirred at room temperature for five days, maintaining the pH at 8.5 with 2N sodium hydroxide. The methanol was removed under vacuum, and the resulting aqueous solution was washed twice with 200 ml of ethyl acetate. The aqueous was applied to a HP-21 resin column. (HP 21 is a cross-linked styrene divinyl benzene copolymer in bead form having a macroreticular structure. It is available from V. G. F. Corporation, 420 Lexington Avenue, New York, N.Y.). The column was washed with two liters of water and then the product eluted with 50% methanol in water. The elutant was concentrated to give product which was triturated with ether, filtered and dried to give 14.1 g (95%) of the title product: mp 204°–210°0 C. (dec.). IR (Nujol) 2200-3600, 1720, 1660, 1580 cm$^{-1}$; NMR (CD$_3$OD) delta 7.45 (s, 5H), 5.20 (s, 2H), 3.50 (m, 2H), 1.4–2.1 (m, 6H); [alpha]$_D$=−16.8 (C=1.0, AcOH).

EXAMPLE 5

N,N'-Dibenzyloxcarbonyl-meso-diaminopimelic acid mono-benzyloxycarbonylcarbazide A suspension of 11.8 g (35 mmol) of meso-diaminopimelic acid-(D)-mono-benzyloxycarbonylcarbazide in 270 ml of dry methylene chloride was treated with 56.8 ml (280 mmol) of bis-trimethylsilylacetamide and stirred at room temperature under nitrogen atmosphere for 18 hours. The reaction solution was cooled to −15° C. and treated over five minutes with 15.0 g (88 mmol) of benzylchloroformate. The reaction was stirred one hour at −15° C. and warmed to room temperature for 18 hours. The solution was acidified with dilute hydrochloric acid, stirred for one hour and then filtered to give 13.6 g (64%) of the title product: mp 141°-145° C. IR (KBr) 3300, 1740, 1715, 1695, 1660 cm$^{-1}$; NMR (CD$_3$OD) delta 7.30 (s, 15H), 5.10 (s, 6H), 4.10 (m, 2H), 1.40-2.00 (m, 6H); [alpha]$_D$= +18.2 (C=0.6, MeOH).

EXAMPLE 6

Benzyloxycarbonyl-meso-diaminopimelic acid-mono-benzyloxycarbonylcarbazide

To a neat solution of 130 ml of thionyl chloride was added 13.0 g (21 mmol) of the title compound of Example 5. The solution was stirred two hours at room temperature, concentrated and dried under high vacuum for one hour. The resulting product was dissolved in 130 ml of acetic acid, treated with 65 ml of 1N hydrochloric acid and stirred at room temperature for 18 hours. The reaction was concentrated, and the resulting slurry was dissolved in 100 ml of water and neutralized with a solution of saturated sodium bicarbonate. The suspension was stirred one hour, filtered, washed with water and dried to give 9.7 g (93%) of the title product: mp 201°-205° C. (dec.). IR (KBr) 3300, 1715, 1690, 1600 cm$^{-1}$; NMR (D$_6$-DMSO) delta 7.2-7.4 (bs, 10H), 5.25 (s, 2H), 5.20 (s, 2H), 4.40 (m, 2H), 1.6-2.5 (m, 6H); [alpha]$_D$= +35.1 (C=0.4, MeOH).

EXAMPLE 7

N-Heptanoyl-D-glutamic acid

A solution of 75.0 g (510 mmol) of D-glutamic acid in one liter of aqueous acetone (50:50) was adjusted to pH 9.0 with 2N sodium hydroxide. The resulting solution was cooled to 10° C. and treated over 45 minutes with 114.2 g (770 mmol) of heptanoyl chloride, maintaining the pH at 9.0 with 2N sodium hydroxide. The reaction was allowed to warm to room temperature for three hours. The acetone was removed under vacuum, and the resulting aqueous solution was acidified with dilute hydrochloric acid and extracted three times with 700 ml portions of ethyl acetate. The extracts were combined, dried over magnesium sulfate, filtered and concentrated. The resulting oil was triturated with hexane to give 109.8 g (83%) of desired product: mp 92°-96° C. IR (Nujol) 3300, 2700-3250, 1720, 1625 cm$^{-1}$; NMR (D$_6$-DMSO) delta 4.20 (m, 1H), 2.28 (t, 2H), 2.20 (t, 2H), 1.85-2.05 (m, 1H), 1.65-1.85 (m, 1H), 1.40-1.60 (m, 2H), 1.15-1.30 (m, 6H), 0.75 (t, 3H); [alpha]$_D$= +9.6 (C=1.0, MeOH).

EXAMPLE 8

N-Heptanoyl-D-glutamic acid-alpha-benzyl ester

A solution of 108.8 g (420 mmol) of N-heptanoyl-D-glutamic acid and 50.6 g (500 mmol) of triethylamine in 135 ml of dimethylformamide was treated with 85.7 g (500 mmol) of benzyl bromide and stirred under nitrogen atmosphere for 60 hours. The reaction was poured onto one liter of ethyl acetate and washed successively with two 500 ml portions each of dilute hydrochloric acid and water. The ethyl acetate was then washed with 500 ml of 1N sodium hydroxide. The basic aqueous layer was acidified with dilute acid and extracted with four 500 ml portions of ethyl acetate. The combined ethyl acetate extracts were treated with excess dicyclohexylamine and stirred 18 hours. The suspension was filtered, slurried in fresh ethyl acetate (400 ml) for two hours, refiltered and dried under vacuum to give 49.1 g of dicyclohexylamine salt. The resulting salt (14.0 g) was stirred in dilute hydrochloric acid, filtered and washed with ethyl acetate. The aqueous filtrate was extracted twice with ethyl acetate, and the organic layers were combined, dried over magnesium sulfate, filtered and concentrated. The resulting oil was triturated with hexane to give 7.9 g (86% from salt) of the title ester: mp 76°-79° C. IR (Nujol) 3300, 2700-3100, 1730, 1700, 1645 cm$^{-1}$; NMR (CDCl$_3$) delta 7.35 (s, 5H), 5.20 (s, 2H), 4.70 (m, 1H), 1.85-2.50 (m, 6H), 1.55-1.70 (m, 2H), 1.10-1.40 (m, 6H), 0.75 (t, 3H); [alpha]$_D$= +27.6 (C=0.6, MeOH).

EXAMPLE 9

N-Heptanoyl-D-glutamic acid-alpha-benzyl-gamma-(N-hydroxysuccinimide)diester

A solution of 7.68 g (22 mmol) of N-heptanoyl-D-glutamic acid-alpha-benzyl ester and 6.1 g (51 mmol) of N-hydroxysuccinimide in 220 ml of ethyl acetate was treated with 22.9 g (51 mmol) of 1-cyclohexyl-3-(2-morpholinoethyl)carbodiimide metho-p-toluene sulfonate. The solution was stirred two days at room temperature and then poured onto 150 ml of water. The layers were separated, and the ethyl acetate portion was washed once with water, once with brine, dried over magnesium sulfate, filtered and concentrated. Triturated with ether gave 8.0 g (82%) of the title diester: mp 85°-89° C. IR (Nujol) 3350, 2800-3000, 1810, 1790, 1745, 1650 cm$^{-1}$; NMR (CDCl$_3$) delta 7.30 (s, 5H), 5.20 (s, 2H), 2.8 (bs, 4H), 2.0-2.7 (m, 6H), 1.50-1.70 (m, 2H), 1.10-1.4 (m, 6H), 0.80 (t, 3H).

EXAMPLE 10

N-Heptanoyl-gamma-D-glutamyl-(alpha-benzyl ester)benzyloxycarbonyl-(D)-meso-diaminopimelic acid(D)-benzyloxycarbonyl-carbazide A solution of 4.22 g (9 mmol) of the title compound of Example 6 and 0.9 g (9 mmol) of N-methylmorpholine in 200 ml of 20% aqueous tetrahydrofuran was treated with 4.0 g (9 mmol) of N-heptanoyl-D-glutamic acid-alpha-benzyl-gamma-(N-hydroxysuccinimide)diester (product of Example 9). The reaction was stirred for two days at room temperature, concentrated and treated with 60 ml of 1N hydrochloric acid and 200 ml of ethyl acetate. The organic layers were combined, washed once with 1N HCl, once with brine, dried over magnesium sulfate, filtered and concentrated. Crystallization from ethyl acetate gave 4.94 g (69%) of title product: mp 139°-141° C. IR (Nujol) 3300-2550, 1680, 1640 cm$^{-1}$; NMR (D$_6$-DMSO) delta 7.30 (bs, 15H), 5.12 (s, 2H), 5.08 (s, 2H), 5.00 (s, 2H), 4.25 (m, 1H), 4.15 (m, 1H), 4.00 (m, 1H), 2.25 (t, 2H), 2.10 (t, 2H), 1.20-2.00 (m, 16H), 0.80 (t, 3H); [alpha]$_D$= +22.4 (C=0.3, MeOH).

EXAMPLE 11

N-Heptanoyl-gamma-D-glutamyl-(alpha-benzyl ester)benzyloxycarbonyl-(D)-meso-diaminopimelic acid-(D)-(benzyloxycarbonylcarbazide)-L-(N-hydroxysuccinimide) ester A solution of 3.70 g (4.6 mmole) of the title compound of Example 10 and 0.64 g (5.52 mmol) of N-hydroxysuccinimide 150 ml of 50% aqueous dioxane was cooled to 10° C. and treated with a single portion of 1.35 g (5.06 mmol) of N,N'-dicyclohexylcarbodiimide. The solution was stirred two hours at 10° C., 18 hours at room temperature, cooled again and filtered. The filtrate was evaporated, redissolved in ethyl acetate, filtered and concentrated. The resulting solid from the filtrate was triturated with ether to give 3.50 g (85%) of the title ester: mp 107°-110° C. IR (KBr) 3600, 3100, 3000, 2950, 1810, 1740, 1710, 1645 cm$^{-1}$; NMR (D$_6$-DMSO) delta 7.35 (bs, 15H), 5.12 (s, 2H), 5.10 (s, 2H), 5.00 (s, 2H), 4.50 (m, 1H), 4.30 (m, 1H), 4.10 (m, 1H), 3.40 (bs, 4H), 1.20–2.40 (m, 20H), 0.85 (t, 3H).

EXAMPLE 12

N-Heptanoyl-gamma-D-glutamyl-(alpha-benzyl ester)benzyloxycarbonyl-(D)-meso-diaminopimelic acid-(D)-(benzyloxycarbonylcarbazide)-L-N-(4-aminobutyl)-5-L-hydantoin A solution of 2.0 g (2.2 mmol) of the product of Example 10 and 0.35 g (2.2 mmol) of 5-(4-aminobutyl)-hydantoin in 200 ml of dimethylformamide was cooled to 5° C. and treated with 0.30 g (2.2 mmol) of 1-hydroxybenzotriazole and 1.68 g (3.96 mmol) of 1-cyclohexyl-3-(2-morpholinoethyl)carbodiimide metho-p-toluene sulphonate. It was stirred one hour at 5° C., then allowed to warm to room temperature for 48 hours and concentrated under high vacuum. The residue was dissolved in 200 ml of ethyl acetate and washed successively with 0.7M aqueous hydrochloric acid, water, saturated aqueous sodium bicarbonate and brine. The organic layer was dried (sodium sulfate), filtered and concentrated to yield 1.80 g of the title product. NMR (D$_6$-DMSO) delta 7.35 (m, 15H), 5.14 (s, 2H), 5.10 (s, 2H), 5.00 (s, 2H), 4.25 (m, 1H), 4.15 (m, 1H), 3.95 (m, 2H), 3.00 (m, 2H), 2.25 (t, 2H), 2.15 (t, 2H), 2.10–1.10 (m, 22H), 0.85 (t, 3H).

EXAMPLE 13

Heptanoyl-gamma-D-glutamyl-L-meso-diaminopimelic acid-N-(4-aminobutyl)-5-L-hydantoin A solution of 0.90 g (0.95 mmol) of the product of Example 12 and 0.2 g of 10% palladium-on-carbon in 100 ml of 20% aqueous acetic acid was hydrogenated under 50 psi (3.52 kg/cm$^2$) of hydrogen for 30 minutes. It was then degassed, filtered and concentrated under reduced pressure. The residue was dissolved in 50 ml of water, the resulting solution acidified to pH 1.5 with concentrated sulfuric acid, cooled to 5° C., stirred and treated with 0.45 g (2.1 mmol) of sodium metaperiodate. The mixture was stirred for one hour, treated with a sufficient volume of saturated aqueous solution of sodium bisulfite to clarify the mixture, then applied to a HP-21 resin column. The column was washed with water and the desired product eluted with 50% aqueous methanol. Evaporation of the elutant gave 0.36 g (65%) of the title product: mp 180° C. (dec.). IR (KBr) 3600–3000, 2950, 2850, 1720, 1640 cm$^{-1}$; NMR (D$_2$O) delta 4.40–4.20 (m, 4H), 3.85 (t, 1H), 3.30 (m, 2H), 2.50 (t, 2H), 2.35 (t, 2H), 2.30–1.2 (m, 22H), 0.90 (t, 3H); [alpha]$_D$=−17 (C=0.5, H$_2$O ).

EXAMPLE 14

N-Heptanoyl-gamma-D-glutamyl-(alpha-benzyl ester)-benzyloxycarbonyl-(D)-meso-diaminopimelic acid-(D)-(benzyloxycarbonylcarbazide)-(L)-N-(3-aminopropyl)pyrrolidine A solution of 2.50 g (3.11 mmol) of protected acid product of Example 10 and 0.60 g (4.67 mmol) of N-(3-aminopropyl)pyrrolidine in 100 ml of dioxane was cooled to 10° C. and treated with 0.63 g (4.67 mmol) of 1-hydroxybenzotriazole. The resulting solution was stirred briefly and treated in a single portion with 1.98 g (4.67 mmol) of 1-cyclohexyl-3-(morpholinoethyl)-carbodiimide metho-p-toluenesulphonate. The reaction was warmed to room temperature, stirred 80 hours and then concentrated. The concentrate was dissolved in ethyl acetate, the solution washed successively with 5% aqueous sodium bicarbonate, water and brine, then dried over sodium sulfate, filtered and concentrated. The white residue was triturated with ether to yield 2.3 g (81%) of the title compound: mp 155°-160° C. (dec.). IR (KBr) 3600–3200, 3100, 2850, 1740, 1670, 1640 cm$^{-1}$; NMR (D$_6$-DMSO) delta 7.35 (m, 15H), 5.15 (s, 2H), 5.10 (s, 2H), 5.00 (s, 2H), 4.30 (m, 1H), 4.10 (m, 1H), 4.00 (m, 1H), 3.50 (bm, 6H), 3.10 (m, 2H), 2.25 (m, 2H), 2.10 (m, 2H), 1.9–1.0 (m, 26H), 0.85 (t, 3H).

EXAMPLE 15

N-Heptanoyl-gamma-D-glutamyl-L-meso-diaminopimelic acid-N-(3-aminopropyl)pyrrolidine Following the procedure of Example 13, 2.10 g (2.30 mmol) of the product of Example 14 in 100 ml of 20% aqueous acetic acid was hydrogenated at 50 psi (3.52 kg/cm$^2$) over 500 mg of 10% Pd/C. The concentrated residue obtained from said hydrogenation was dissolved in 50 ml of water, the solution acidified to pH 2.0 and treated with 1.08 g (5.0 mmol) of sodium metaperiodate. A yield of 0.95 g (76%) of the title product was obtained: mp 160° C. (dec.). IR (KBr) 3600–3200, 2850, 1660, 1600 cm$^{-1}$; NMR (D$_2$O) delta 4.25 (m, 2H), 3.80 (m, 1H), 3.70 (m, 2H), 3.35 (m, 2H), 3.15 (m, 2H), 2.40 (m, 4H), 2.30–1.25 (m, 22H), 0.90 (t, 3H), [alpha]D=−1.25 (C=0.4, H$_2$O ).

EXAMPLE 16

N-Heptanoyl-gamma-D-glutamyl-(alpha-benzyl ester)-benzyloxycarbonyl-D-meso-diaminopimelic acid-D-(benzyloxycarbonylcarbazide)-L-[N-(4-benzyloxycarbonylpiperidine)]

A solution of 1.30 g (1.62 mmol) of the product of Example 10 and 0.97 g (2.43 mmol) of benzylisonipecotate p-toluenesulphonate in 100 ml of dry tetrahydrofuran was cooled to 0° C. and treated sequentially with 0.24 g (2.43 mmol) of N-methylmorpholine and 0.33 g (2.43 mmol) of 1-hydroxybenzotriazole. To the resulting solution was added 1.03 g (2.43 mmol) of 1-cyclohexyl-3-(2-mor-pholinoethyl)carbodiimide metho-p-toluenesulphonate. The reaction was stirred 18 hours at room temperature, concentrated, dissolved in ethyl acetate and washed sequentially with 2.5% aqueous hydrochloric acid, water and brine. The resulting organic layer was separated, dried over sodium sulfate, filtered and evaporated and triturated with hexane to give 0.74 g (46%) of the title compound. NMR (D$_6$-

DMSO) delta 7.30 (bs, 20H), 5.12 (s, 4H), 5.08 (s, 2H), 5.00 (s, 2H), 4.60 (n, 1H), 4.20 (m, 1H), 4.00 (m, 1H), 3.30 (bs, 4H), 2.30–1.10 (m, 25H), 0.85 (t, 3H).

EXAMPLE 17

N-Heptanoyl-gamma-D-glutamyl-L-meso-diaminopimelic acid-1-(4-carboxypiperidine)

The product of Example 16 (0.38 g, 0.39 mmol) was hydrogenated and the reaction worked up according to the procedure of Example 13. The following quantities of reactants and reaction conditions were used: 100 mg of 10% Pd/C; 25 ml water; pH 1.5; 0.18 g (0.85 mmol) of sodium metaperiodate. Yield of the title product was 0.17 g (80%): mp 204° C. (dec.). IR (KBr) 3600–3000, 2850, 1720, 1640, 1520 cm$^{-1}$; NMR (D$_2$O) delta 4.35 (m, 2H), 4.10 (m, 1H), 3.85 (t, 1H), 3.40 (m, 1H), 3.00 (m, 1H), 2.80 (m, 1H), 2.50 (t, 2H), 2.35 (t, 2H), 2.30–1.20 (m, 21H), 9.90 (t, 3H).

EXAMPLE 18

N-Heptanoyl-gamma-D-glutamyl-(alpha-benzyl ester)benzyloxycarbonyl-D-meso-diaminopimelic acid-D-(benzyloxycarbonylcarbazide)-L-1-(4-methylpiperazine)

A solution of 2.50 g (3.11 mmol) of the product of Example 10, 0.47 g (4.67 mmol) of N-methylpiperazine and 0.63 g (4.6 mmol) of 1-hydroxybenzotriazole in 100 ml of dry tetrahydrofuran was cooled to 5° C. and treated in a single portion with 1.98 g (4.67 mmol) of 1-cyclohexyl-3-(2-morpholinoethyl)carbodiimide metho-p-toluenesulphonate. The solution was stirred at room temperature for 18 hours, then concentrated and the residue dis-solved in ethyl acetate. The ethyl acetate solution was washed successively with 5% aqueous sodium bicarbonate, water and brine, and the organic layer dried over sodium sulfate, filtered and concentrated. The resulting solid was triturated with hexane, filtered and dried to give 2.06 g (72%) of the title compound. IR (KBr) 3600–3100, 3050, 2950, 1740, 1640 cm$^{-1}$; NMR (D$_6$-DMSO) delta 7.30 (m, 15H), 5.15 (s, 2H), 5.10 (s, 2H), 5.00 (s, 2H), 4.65 (m, 1H), 4.25 (m, 1H), 4.00 (m, 1H), 3.40 (m, 8H), 3.35 (s, 3H), 2.30–1.10 (m, 20H), 0.85 (t, 3H).

EXAMPLE 19

N-Heptanoyl-gamma-D-glutamyl-L-meso-diaminopimelic acid-1-(4-methylpiperazine)

Hydrogenation at 50 psi (3.52 kg/cm$^2$) for one hour of 1.70 g (1.86 mmol) of the product of Example 18 over 400 mg of 10% Pd/C in 100 ml of 20% aqueous acetic acid and work-up of the mixture according to Example 13 [50 ml water, pH 2.0, 0.87 g (4.09 mmol) sodium meta-periodate] afforded 0.71 g (74%) of the title product: mp 210° C. IR (KBr) 3600–3100, 1640, 1560 cm$^{-1}$; NMR (D$_2$O) delta 4.30 (m, 2H), 3.85 (t, 1H), 3.70 (m, 4H), 3.25 (m, 4H), 3.05 (s, 3H), 2.40 (t, 2H), 2.35 (t, 2H), 2.30–1.10 (m, 16H), 0.90 (t, 3H); [alpha]$_D$= −15.5 (C=1.0, H$_2$O ).

EXAMPLE 20

N-Heptanoyl-gamma-D-glutamyl-(alpha-benzyl ester)-benzyloxycarbonyl-D-meso-diaminopimelic acid-D-(benzyloxycarbonylcarbazide)N-[1-(3-aminopropyl)-2-pyrrolidinone]

A solution of 2.50 g (3.11 mmol) of the Example 10 product and 0.61 g (4.6 mmol) of N-(3-aminopropyl)-2-pyrrolidinone in 70 ml of tetrahydrofuran was treated with 0.62 g (4.60 mmol) of 1-hydroxybenzotriazole, cooled to 5° C. and treated with 1.95 g (4.6 mmol) of 1-cyclohexyl-3-(2-morpholinoethyl)carbodiimide metho-p-toluenesulphonate. The resulting solution was stirred for 16 hours at room temperature, concentrated and redissolved in 200 ml of ethyl acetate. The solution was washed successively with 0.7N hydrochloric acid, water, 5% aqueous sodium bicarbonate, water and brine. The organic layer was dried over sodium sulfate, filtered and concentrated. The solid was triturated with ether to give 2.46 g (86%) of the title product: mp 201–203° C. IR (KBr) 3600–3200, 2950, 1740, 1680, 1640, 1540 cm$^{-1}$; NMR (D$_6$-DMSO) delta 7.30 (bs, 15H), 5.15 (s, 2H), 5.10 (s, 2H), 5.00 (s, 2H), 4.25 (m, 1H), 4.15 (m, 1H), 4.00 (m, 1H), 4.25 (t, 2H), 4.15 (t, 2H), 4.00 (m, 2H), 2.30–2.00 (m, 6H), 2.05–1.10 (m, 20H), 0.85 (t, 3H).

EXAMPLE 21

N-Heptanoyl-gamma-D-glutamyl-L-meso-diaminopimelic acid-L-N-[(3-aminopropyl)-2-pyrrolidinone]

The product of Example 20 (2.25 g, 2.4 3 mmol) and 0.40 g of 10% Pd/C in 200 ml of 20% aqueous acetic acid was hydrogenated at 50 psi (3.52 kg/cm$^2$) for one hour according to the procedure of Example 13. The mixture was worked up at pH 1.5, treated with 1.14 g (5.35 mmol) of sodium metaperiodate per the Example 13 procedure to give 0.81 g (60%) of the title compound: mp 190° C. (dec.). IR (KBr) 3600–3100, 2950, 1640, 1540 cm$^{-1}$; NMR (D$_2$O) delta 4.30 (m, 1H), 4.20 (m, 1H), 4.00 (m, 1H), 3.45 (t, 2H), 3.25 (t, 2H), 3.20 (t, 2H), 2.40–2.20 (m, 6H), 2.30–1.10 (m, 20H), 0.85 (t, 3H); [alpha]D= −19.0 (C=0.5, H$_2$O ).

EXAMPLE 22

N-Heptanoyl-gamma-D-glutamyl-(alpha-benzyl ester)-D-benzyloxycarbonyl-D-(benzyloxycarbonylcarbazide)-L-meso-diaminopimelic acid-N-[2-(2-aminoethyl)-pyridine]

A solution of 3.0 g (3.73 mmol) of the product of Example 10, 0.68 g (5.60 mmol) of 2-(2-aminoethyl)-pyridine, 0.76 g (5.60 mmol) 1-hydroxybenzotriazole in 100 ml of dry tetrahydrofuran was cooled to 5° C. and treated in one portion with 2.37 g (5.60 mmol) of 1-cyclohexyl-3-(2-morpholinoethyl)carbodiimide metho-p-toluenesulphonate. The solution was stirred for 18 hours at room temperature, concentrated and the residue dissolved in 100 ml of ethyl acetate. The organic solution was washed successively with 5% aqueous sodium bicarbonate, water and brine, then dried over sodium sulfate, filtered, concentrated and tri-turated with ether to give 3.14 g (94%) of the title compound.

EXAMPLE 23

N-Heptanoyl-gamma-D-glutamyl-L-meso-diaminopimelic acid-N-[2-(2-aminoethyl)pyridine]

The Example 22 product (3.00 g, 3.35 mmol) in 200 ml of 10% aqueous acetic acid was hydrogenated over 750 mg of 10% Pd/C for 7 hours at 50 psi (3.52 kg/cm$^2$) and worked up according to the Example 13 procedure [pH 1.5, 1.58 g (7.37 mmol) sodium metaperiodate] to give 0.76 g (42%) of the title compound: mp 180° C. (dec.). IR (KBr) 3600–3100, 2950, 1640, 1545 cm$^{-1}$; NMR (D$_2$O) delta 8.70 (d, 1H), 8.50 (t, 1H), 7.90 (t, 2H), 4.25 (m, 1H), 4.15 (m, 1H), 3.80 (m, 3H), 3.35 (t, 2H), 2.40 (m, 4H), 2.20–1.20 (m, 16H), 0.90 (t, 3H), [alpha]D=−13.6 (C=0.5, H$_2$O ).

EXAMPLE 24

N-Heptanoyl-gamma-D-glutamyl-(alpha-benzyl ester)D-benzyloxycarbonyl-D-benzyloxycarbonylcarbazide-L-meso-diaminopimelic acid-N-(2-aminothiazole)

A solution of 2.00 g (2.22 mmol) of the product of Example 11, 0.27 g (2.66 mmol) of 2-aminothiazole and 50 mg of 1-hydroxybenzotriazole in 200 ml of dioxane was stirred for 48 hours at room temperature. The resulting suspension was filtered, washed with ether and dried to give 1.23 g (62%) of the title product. NMR (D$_6$-DMSO) delta 7.50 (d, 1H), 7.30 (m, 15H), 7.25 (d, 1H), 5.15 (s, 2H), 5.10 (s, 2H), 5.00 (s, 2H), 4.50 (m, 1H), 4.30 (m, 1H), 4.00 (m, 1H), 2.30 (m, 2H), 2.15 (t, 2H), 2.10–1.10 (m, 16H), 0.90 (t, 3H).

EXAMPLE 25

N-Heptanoyl-gamma-D-glutamyl-L-meso-diaminopimelrc acid-N-(2-aminothiazole)

A solution of 1.00 g (1.13 mmol) of the product of Example 24, 25 ml of 10% trifluoromethanesulfonic acid in trifluoroacetic acid, 1.83 g (16.9 mmol) of anisole, and 6 ml of dimethylsulfide was stirred 2 hours at room temperature. The resulting mixture was diluted with 250 ml of water, concentrated and the residue redissolved in 50 ml of water. The solution was acidified to pH=1.5 with sulfuric acid, cooled to 5° C. and treated with 0.54 g (2.50 mmol) of sodium metaperiodate. The resulting reaction mixture was stirred 1 hour at 5° C., clarified with saturated sodium bisulfite solution and loaded onto a 40 ml column of HP-21 resin. The column was washed with 1 liter of water and the product eluted with 60% aqueous methanol. The fractions containing the desired product were com-bined, concentrated and the resulting solid was lyophi-lized to give 0.34 g (58%) of the title product: mp 175° C. (dec). IR (KBr) 3600–3000, 2950, 1640, 1540 cm$^{-1}$; NMR (D$_2$O) delta 7.55 (d, 1H), 7.25 (d, 1H), 4.55 (m, 1H), 4.30 (m, 1H), 3.70 (m, 1H), 2.40 (t, 2H), 2.25 (t, 2H), 2.20–1.20 (m, 16H), 0.90 (t, 3H).

EXAMPLE 26

N-Heptanoyl-gamma-D-glutamyl-(alpha-benzyl ester)D-benzyloxycarbonyl-D-benzyloxycarbonylcarbazide-L-meso-diaminopimelic acid-N-[2-(2-ethylaminoethyl)lridine]

A solution of 1.50 g (1.87 mmol) of the Example 10 product, 0.28 g (2.06 mmol) of 1-hydroxybenzotriazole and 0.42 g (2.80 mmol) of 2-(2-ethylaminoethyl)pyridine in 100 ml of anhydrous tetrahydrofuran was cooled to 10° C. and treated with 0.425 g (2.06 mmol) of dicyclohexylcarbodiimide. The resulting solution was stored 1 hour at 10° C. and allowed to warm to room temperature for 30 hours. The resulting suspension was filtered, the filtrate concentrated and redissolved in 200 ml of ethyl acetate. The ethyl acetate solution was washed successively with 200 ml each of 2.5% aqueous hydrochloric acid, 5% aqueous sodium bicarbonate, water and brine. The solution was then dried over sodium sulfate, filtered and concentrated. The resulting solid was triturated with hexane, and filtered to give 0.86 g (49%) of the title compound: mp 180°–183° C. IR (KBr) 3050, 2920, 2850, 1740, 1640 cm ; NMR (D$_6$-DMSO) delta 8.40 (d, 1H), 8.10 (m, 1H), 7.70 (t, 2H), 7.35 (m, 15H), 5.15 (s, 2H), 5.10 (s, 2H), 5.05 (s, 2H), 4.25 (m, 1H), 4.15 (m, 1H), 3.80 (m, 1H), 3.30 (m, 4H), 2.5–0.9 (m, 24H), 0.85 (t, 3H).

EXAMPLE 27

N-Heptanoyl-gamma-D-glutamyl-L-meso-diaminopimelic acid-N-[2-(2-ethylaminoethyl)pyridine]

A solution of 0.75 g (0.80 mmol) of the product of Example 26 and 275 mg of 10% palladium-on-carbon catalyst in 50 ml of 20% aqueous acetic acid was hydrogenated at room temperature under 50 psi (3.52 kg/cm$^2$) of hydrogen for 5 hours. The solution was filtered and evaporated to dryness. The residue was dissolved in 50 ml of water acidified to pH=2.0 with sulfuric acid, cooled to 10° C. and treated with 0.38 g (1.76 mmol) of sodium metaperiodate. The reaction was stirred 1 hour, clarified with saturated sodium bisulfite and applied to a 20 ml column of HP-21 resin. The column was washed with 200 ml of water and the product was eluted with 400 ml of 50% aqueous methanol. The methanol-water fractions were concentrated, the residue dissolved in 50 ml water and lyophilized to give 0.22 g (51%) of the desired product: mp 70° C. (dec.). IR (KBr) 3600–3000, 2950, 2850, 1640, 1520 cm$^{-1}$; NMR (D$_2$O) delta 8.65 (d, 1H), 8.40 (t, 1H), 7.85 (t, 2H), 4.20 (m, 1H), 3.90 (m, 1H), 3.75 (m, 1H), 3.50 (m, 2H), 3.30 (t, 2H), 2.30 (m, 6H), 2.20–1.10 (m, 19H), 0.90 (t, 3H); [alpha]$_D$=−18.2 (C=0.5, H$_2$O ).

EXAMPLE 28

N-Heptanoyl-gamma-D-glutamyl-(alpha-benzyl ester)-D-benzyloxycarbonyl-D-benzyloxycarbonylcarbazide-L-mesodiaminopimelic acid-N-[2-(2-methylaminoethyl)pyridine]

A solution of 2.00 g (2.22 mmol) of the product of Example 11, 0.05 g of 1-hydroxybenzotriazole and 0.36 g (2.6 mmol) of 2-(2-methylaminoethyl)pyridine in 200 ml of chloroform was refluxed for 2 hours, cooled and concentrated. The residue was dissolved in 200 ml of ethyl acetate and washed successively with 200 ml of 2.5% aqueous hydrochloric acid, water, 5% aqueous bicarbonate and brine, then dried over sodium sulfate, filtered and concentrated. The resulting solid was triturated with ether to give 1.22 g (81%) of the title compound mp 105°–109° C. IR (KBr) 3600–3000, 3050, 2950, 1740, 1640 cm$^{-1}$; NMR (D$_6$-DMSO) delta 8.25 (d, 1H), 8.10 (t, 1H), 7.65 (t, 2H), 7.35 (m, 15H), 5.10 (s, 2H), 5.00 (s, 2H), 4.60 (m, 1H), 4.30 (m, 1H), 4.00 (m, 1H), 3.40 (s, 3H), 3.10–2.90 (m, 5H), 2.25 (m, 2H), 2.10 (t, 2H), 2.10–1.10 (m, 16H), 0.85 (t, 2H).

EXAMPLE 29

N-Heptanoyl-gamma-D-glutamyl-L-meso-diaminopimelic acid-N-[2-(2-methylaminoethyl)pyridine]

A solution of 1.00 g (0.9 mmol) of the Example 28 product in 50 ml of 20% aqueous acetic acid was treated with 0.25 g of 10% palladium-on-carbon and hydrogenated at 50 psi (3.52 kg/cm$^2$) for 1 hour. The solution was degassed, filtered and concentrated. The residue was dissolved in 50 ml of water, acidified to pH=1.5 with sulfuric acid, cooled to 10° C. and treated with 0.51 g (2.4 mmol) of sodium metaperiodate. The resulting mixture was stirred 1 hour, clarified with aqueous saturated sodium bisulfite and applied to a 100 ml column of HP-21 resin. The column was washed with 200 ml of water and the product was eluted with 500 ml of 50% aqueous methanol. The methanol-water fractions were concentrated and the resulting solid was redissolved in water and lyophilized to give 0.29 g (58%) of desired product: mp 185° C. (dec.). IR (KBr) 3600–3000, 2940, 1640, 1540 cm$^{-1}$; NMR (D$_2$O) delta 8.60 (d, 1H), 8.35 (t, 1H), 7.85 (d, 1H), 7.75 (m, 1H), 4.60 (m, 1H), 4.20 (m, 1H), 3.90 (m, 1H), 3.70 m, 2H), 3.30 (t, 2H), 3.18 (s, 3H), 2.25 (t, 4H), 2.10–1.10 (m, 16H), 0.85 (t, 3H); [alpha]$_D$= +26.0 (C=0.5, H$_2$O ).

EXAMPLE 30

N-Heptanoyl-gamma-D-glutamyl-(alpha-benzyl ester)D-benzyloxycarbonyl-D-benzyloxycarbonylcarbazide-L-meso-diaminopimelic acid-N-[4-(3-aminopropyl)morpholine]

A solution of 2.00 g (2.49 mmol) of the product of Example 11, 0.41 g (3.00 mmol) of N-3-aminopropylmorpholine in 75 ml of tetrahydrofuran was cooled to 0° C. and treated with 1.27 g (3.00 mmol) of 1-cyclohexyl-3-(2-morpholinoethyl)carbodiimide metho-p-toluene-sulphonate. The solution was stirred for 30 hours and evaporated to dryness. The residue was dissolved in 250 ml of ethyl acetate and washed successively with 250 ml of 2.5% aqueous hydrochloric acid, water, 5% aqueous sodium bicarbonate, water and brine. The washed solution was dried over sodium sulfate, filtered, con-centrated and the resulting solid triturated with ether and recrystallized from ethyl acetate to give 1.33 g (57%) of product: mp 165° C. (dec.). IR (KBr) 3600–3000, 2950, 2850, 1720, 1680, 1640, 1540 cm$^{-1}$; NMR (D$_6$-DMSO) delta 7.35 (m, 15H), 5.15 (s, 2H), 5.10 (s, 2H), 5.00 (s, 2H), 4.30 (m, 1H), 4.18 (m, 1H), 4.00 (m, 1H), 3.50 (t, 4H), 3.40 (m, 2H), 3.10 (m, 2H), 2.30–1.10 (m, 26H), 0.85 (t, 3H).

EXAMPLE 31

N-Heptanoyl-gamma-D-glutamyl-L-meso-diaminopimelic acid-N-(4-gamma-aminopropyl)morpholine Catalytic hydrogenation of 1.20 g (1.30 mmol) of the product of Example 30 in 100 ml of 20% aqueous acetic acid over 0.40 g of 10% Pd/C at 50 psi (3.52 kg/cm$^2$) for 24 hours and work-up of the reaction mixture according to the procedure of Example 29 but using 0.60 g (2.84 mmol) of sodium metaperiodate and 60% aqueous methanol for elution (one liter) gave 0.27 g (37%) of the title product: mp 185° C. (dec.). IR (KBr) 3600–3000, 2950, 1640, 1540 cm$^{-1}$; NMR (D$_2$O) delta 4.20–4.00 (m, 3H), 3.90–3.10 (m, 12H), 2.35 (t, 2H), 2.25 (t, 2H), 2.20–1.10 (m, 18H), 0.90 (t, 3H); [alpha]$_D$= −16.6 (C=0.5, H$_2$O ).

EXAMPLE 32

N-Heptanoyl-gamma-D-glutamyl-(alpha-benzyl ester)D-benzyloxycarbonyl-D-benzyloxycarbonylcarbazide-L-meso-diaminopimelic acid-N-morpholine A solution of 1.50 g (1.87 mmol) of the product of Example 10, 0.37 g (4.24 mmol) of morpholine and 0.38 g (2.81 mmol) of 1-hydroxybenzotriazole in 100 ml of tetrahydrofuran was cooled to 0° C. and treated with 1.60 g (3.74 mmol) of 1-cyclohexyl-3-(2-morpholinoethyl)carbodiimide metho-p-toluenesulfonate. The resulting reaction mixture was stirred for 30 hours at room temperature, concentrated and the residue redissolved in 100 ml of ethyl acetate. The solution was washed successively with 100 ml each of 2.5% aqueous hydrochloric acid, water, 5% aqueous sodium bicarbonate, water and brine. The solution was dried over sodium sulfate, filtered and concentrated. The resulting solid was triturated with hexane, filtered and dried to give 1.15 g (70%) of the title compound. IR (KBr) 3600–3000, 3050, 2950, 1740, 1640, 1540 cm$^{-1}$; NMR (D$_6$-DMSO) delta 7.25 (m, 15H), 5.10 (s, 2H), 5.05 (s, 2H), 5.00 (s, 2H), 4.80 (m, 1H), 4.55 (m, 1H), 4.30 (m, 1H), 3.70–3.50 (m, 3H), 2.30–2.10 (m, 4H), 2.10–1.10 (m, 16H), 0.85 (t, 3H).

EXAMPLE 33

N-Heptanoyl-gamma-D-glutamyl-L-mesodiaminopimelic acid-N-morpholine

Repetition of the procedure of Example 30 but using 1.00 g (1.15 mmol) of the product of Example 31, 50 ml of 20% aqueous acetic acid, 0.25 g of 10% Pd/C, 0.54 g (2.53 mmol) of sodium metaperiodate and 400 ml of 50% aqueous methanol for elution of product gave 0.29 g (50%) of the title product: mp 170° C. (dec.). IR (KBr) 3600–3000, 2920, 1640, 1550 cm$^{-1}$; NMR (D$_2$O) delta 4.40–4.10 (m, 3H), 3.70–3.20 (m, 8H), 2.20 (t, 2H), 2.10 (t, 2H), 2.10–1.10 (m, 16H), 0.85 (t, 3H); [alpha]$_D$= −15.0 (C=0.5, H$_2$O ).

EXAMPLE 34

N-Heptanoyl-gamma-D-glutamyl-(alpha-benzyl ester)-D-benzyloxycarbonyl-D-benzyloxycarbonylcarbazide-L-meso-diaminopimelic acid-N-pipecolinic acid A solution of 0.32 g (2.44 mmol) of pipecolinic acid and 0.25 g (2.44 mmol) of N-methylmorpholine in 100 ml of 20% aqueous dioxane was treated with 2.00 g (2.22 mmol) of the Example 11 product and stirred for 24 hours at room temperature. The solution was evaporated, redissolved in 200 ml of ethyl acetate and washed successively with 2.5% aqueous hydrochloric acid, water and brine. The ethyl acetate solution was dried over sodium sulfate, filtered, concentrated and the resulting solid triturated with ether to give 1.37 g (61%) of the title product. IR (KBr) 3600–3000, 3050, 2950, 1740, 1660, 1640 cm$^{-1}$; NMR (D-DMSO) delta 7.35 (m, 15H), 5.15 (s, 2H), 5.10 (s, 2H), 5.00 (s, 2H), 4.30 (m, 1H), 4.15 (m, 1H), 4.00 (m, 2H), 2.50 (m, 2H), 2.25 (t, 2H), 2.15 (t, 2H), 2.10–1.10 (m, 22H), 0.85 (t, 3H).

EXAMPLE 35

-Heptanoyl-gamma-D-glutamyl-L-mesodiaminopimelic acid-N-pipecolinic acid

The product of Example 34 (0.97 g, 1.06 mmol) was deblocked according to the procedure of Example 25 using the following reaction conditions 2.4 g (15.9 mmol) of trifluoromethane sulfonic acid, 13 ml of trifluoroacetic acid, 1.72 g (15.9 mmol) of anisole and 31.8 mmol of dimethyl sulfide, 24 hours, 0.46 g (2.12 mmol) of sodium metaperiodate. The pH of the reaction was adjusted to 3.0 prior to passing it through 200 ml of HP-21 resin. Yield=0.18 g (31%) of title product. IR (KBr) 3600–3000, 2850, 1640, 1550 cm$^{-1}$; NMR (D$_2$O) delta 4.30 (m, 4H), 2.75 (t, 2H), 2.40 (t, 2H), 2.30 (t, 2H), 2.20–1.20 (m, 22H), 0.85 (t, 3H).

EXAMPLE 36

N-Heptanoyl-gamma-D-glutamyl-(alpha-benzyl ester)D-benzyloxycarbonyl-D-benzyloxycarbonylcarbazide-L-meso-diaminopimelic acid-N-(ethyl isonipecotate)

A solution of 2.00 g (2.49 mmol) of the product of Example 10, 0.59 g (3.74 mmol) of ethyl isonipecotate and 0.77 g (4.98 mmol) of 1-hydroxybenzotriazole in a 30/70 mixture of dioxane and tetrahydrofuran was cooled to 5° C. and treated in one portion with 2.11 g (4.98 mmol) 1-cyclohexyl-3-(2-morpholinoethyl)carbodiimide metho-p-toluenesulfonate. The solution was stirred 24 hours at room temperature, concentrated and redissolved in 200 ml of ethyl acetate. The resulting solution was washed successively with 2.5% aqueous hydrochloric acid, water and brine, then dried over sodium sulfate, filtered and concentrated. The residue was chromatographed on silica gel (hexane/ethyl acetate) to give 0.76 (32%) of the title product: mp 89°–94° C. IR (KBr) 3600–3000, 3050, 2950, 1740, 1640, 1525 cm$^{-1}$; NMR (D$_6$-DMSO) delta 7.35 (m, 15H), 5.15 (s, 2H), 5.10 (s, 2H), 5.05 (s, 2H), 4.70 (m, 1H), 4.30 (m, 1H), 4.10 (m, 2H), 3.80 (m, 1H), 3.10–2.50 (m, 4H), 2.20–2.10 (m, 5H), 2.10–1.10 (m, 23H), 0.90 (t, 3H).

EXAMPLE 37

N-Heptanoyl-gamma-D-glutamyl-L-meso-diamino pimelic acid-N-(ethyl isonipecotate)

Following the procedure of Example 31, 0.42 g (0.45 mmol) of the Example 36 product was catalytically hydrogenated using 100 ml of 20% aqueous acetic acid, 0.1 g of 10% Pd/C, 50 psi (3.2 kg/cm$^2$) for 30 minutes; 0.19 g (0.9 mmol) of sodium metaperiodate and 50% aqueous methanol for elution of product. Yield=0.20 g (77%) of title compound. IR (KBr) 3600–3000, 2950, 1740, 1640, 1550 cm$^{-1}$; NMR (D$_2$O) delta 4.35 (m, 1H), 4.20 (q, 2H), 4.0 (m, 1H), 3.80 (m, 1H), 3.30 (m, 2H), 2.90 (m, 2H), 2.70 (m, 1H), 2.40 (t, 2H), 2.30 (t, 2H), 2.20–1.20 (m, 23H), 0.85 (t, 3H); [alpha]D= −17.5 (C=1.0, H$_2$O ). EXAMPLE 38

The procedures of Examples 12 and 13 are repeated but using the appropriate amine of formula

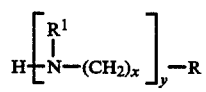

to provide the following compounds:

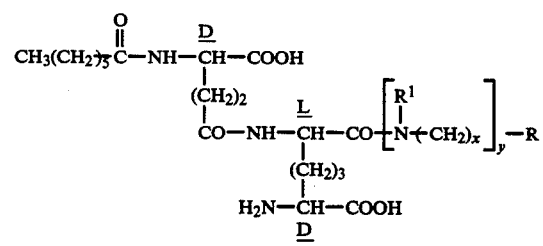

| Y | X | R$^1$ | R |
|---|---|---|---|
| 1 | 2 | H | 1-pyrrolidinyl |
| 1 | 5 | H | 1-pyrrolidinyl |
| 1 | 1 | H | 2-thienyl |
| 1 | 1 | H | 4-piperidinyl |
| 1 | 1 | H | 3-(5-methylisoxazolyl) |
| 1 | 1 | H | 5-(3-methylisoxazolyl) |
| 1 | 1 | H | 2-pyridinyl |
| 1 | 1 | H | 4-pyridinyl |
| 1 | 3 | H | 1-(2-methylpiperidinyl) |
| 1 | 2 | H | 4-pyridinyl |
| 1 | 1 | H | 3-pyridinyl |
| 1 | 0 | H | 2-imidazolyl |
| 1 | 0 | H | 2-thiazolyl |
| 1 | 0 | H | 1-(4-methylpiperazinyl) |
| 1 | 0 | H | 2-(4-methylpyrimidinyl) |
| 1 | 0 | H | 2-nicotinyl |
| 1 | 0 | H | 6-nicotinyl |

-continued

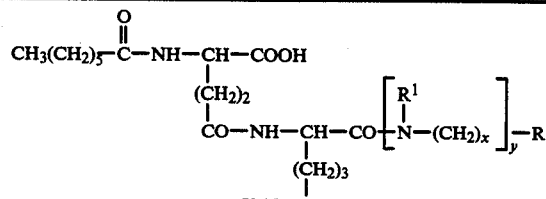

| Y | X | R$^1$ | R |
|---|---|---|---|
| 1 | 0 | H | 2-(5-methylpyridinyl) |
| 1 | 0 | H | 2-(6-methylpyridinyl) |
| 1 | 0 | H | 3-pyrazolyl |
| 1 | 0 | H | 2-pyrimidinyl |
| 1 | 0 | H | 1-pyrrolidinyl |
| 0 | — | — | 1-pyrrolidinyl |
| 0 | — | — | 4-thiomorpholinyl |
| 0 | — | — | 1-piperidinyl |
| 1 | 2 | H | 4-morpholinyl |
| 1 | 2 | H | 1-piperidinyl |
| 1 | 1 | CH$_3$ | 3-pyridinyl |
| 1 | 1 | H | 2-tetrahydrofuryl |
| 1 | 1 | H | 2-furyl |
| 0 | — | — | 1-(3-carboethoxypiperidinyl) |
| 0 | — | — | 1-(2-carboethoxypiperidinyl) |
| 0 | — | — | 1-(2-methylpiperidinyl) |
| 0 | — | — | 1-(3-methylpiperidinyl) |
| 0 | — | — | 1-(4-methylpiperidinyl) |
| 1 | 0 | H | 3-(1-ethylpiperidinyl) |
| 0 | — | — | 1-(4-phenylpiperidine) |
| 1 | 0 | H | thiazolinyl |

I claim:

1. A compound having the formula $$CH_3(CH_2)_5\overset{O}{\overset{\|}{C}}-NH-\overset{D}{\underset{|}{CH}}-COOH$$
$$\underset{|}{(CH_2)_2}$$
$$CO-NH-\overset{L}{\underset{|}{CH}}-CO-[\underset{|}{\overset{R^1}{N}}-(CH_2)_x]_y-R$$
$$\underset{|}{(CH_2)_3}$$
$$H_2N-\underset{\underline{D}}{CH}-COOH$$

or a pharmaceutically acceptable salt thereof wherein
R is an unsubstituted or substituted 5- or 6-membered heterocyclyl moiety selected from the group consisting of imidazolidinyl, pyrrolidinyl, piperidinyl, piperazinyl, pyridinyl, morpholinyl, thienyl, imidazolyl, pyrazolyl, thiomorpholinyl, thiazolyl, thiazolinyl, furyl, tetrahydrofuryl, pyrimidinyl and isoxazolyl;

and wherein the substituent is selected from the group consisting of methyl, oxo, carboxy or carbo(C$_{1-4}$ alkoxy);

R$^1$ is hydrogen or (C$_{1-2}$)alkyl;

x is 0 or an integer from 1 to 5; and y is 0 or 1; pk provided that when y is 0, said heterocyclyl moiety is linked to the —CO— group at its N atom.

2. A compound according to claim 1 wherein y is 0.

3. A compound according to claim 2 wherein said heterocyclyl moiety has one N atom and is pyridinyl, piperidinyl or pyrrolidinyl.

4. A compound according to claim 3 wherein said heterocyclyl moiety is a substituted heterocyclyl moiety.

5. A compound according to claim 4 wherein said heterocyclyl moiety is a carboxy substituted pyridinyl or piperidinyl moiety.

6. A compound according to claim 2 wherein said heterocyclyl moiety has two N atoms and is imidazolyl, imidazolidinyl, pyrazolyl, piperazinyl or pyrimidinyl.

7. A compound according to claim 6 wherein said heterocyclyl moiety is a substituted heterocyclyl moiety.

8. The compound according to claim 7 wherein said substituted heterocyclyl moiety is 4-methylpiperazin-1-yl.

9. A compound according to claim 2 wherein said heterocyclyl moiety has one N and one O hetero atom and is isoxazolyl or morpholinyl.

10. The compound according to claim 9 wherein said heterocyclyl moiety is morpholin-4-yl.

11. A compound according to claim 1 wherein y is 1.

12. A compound according to claim 11 wherein x is O and $R^1$ is hydrogen.

13. The compound according to claim 12 wherein R is a 5-membered heterocyclyl moiety having one N and one S atom and is thiazol-2-yl.

14. The compound according to claim 11 wherein x is 2, $R^1$ is methyl and R is pyrid-2-yl.

15. A compound according to claim 11 wherein $R^1$ is hydrogen, and R is 5-L-hydantoin.

16. The compound according to claim 15 wherein x is 4.

17. A pharmaceutical composition in unit dosage form comprising a pharmaceutically acceptable carrier and an antiinfective or immunostimulant effective amount of a compound of claim 1.

18. A method for treating an infection in a human suffering therefrom which comprises administering to said human antiinfective amount of a compound of claim 1.

* * * * *